(12) United States Patent
Hsue

(10) Patent No.: US 6,412,493 B1
(45) Date of Patent: Jul. 2, 2002

(54) VAGINAL ENDOSCOPIC SURGICAL BLOCKAGE TO THE INNERVATION OF PRESCARAL NERVE PLEXUS

(76) Inventor: Chao Song Hsue, P.O. Box 2103, Taichung (TW)

( * ) Notice: Subject to any disclaimer, the term of this patent is extended or adjusted under 35 U.S.C. 154(b) by 15 days.

(21) Appl. No.: 09/612,837

(22) Filed: Jul. 10, 2000

(51) Int. Cl.[7] ............................................... A61B 19/00
(52) U.S. Cl. ................................................... 128/898
(58) Field of Search ......................... 128/898; 606/119, 606/13, 14, 15, 16, 17

(56) References Cited

U.S. PATENT DOCUMENTS

| 5,258,026 A | * | 11/1993 | Johnson et al. | ............. | 128/898 |
| 5,458,131 A | * | 10/1995 | Wilk | ........................... | 128/898 |
| 5,503,163 A | * | 4/1996 | Boyd | ........................... | 128/849 |
| 5,830,151 A | * | 11/1998 | Hadzic et al. | ............... | 600/554 |
| 6,156,006 A | * | 12/2000 | Bronsens et al. | ........... | 604/104 |

\* cited by examiner

*Primary Examiner*—Corrine McDermott
*Assistant Examiner*—Thomas Barrett
(74) *Attorney, Agent, or Firm*—Rosenberg, Klein & Lee

(57) ABSTRACT

The preferred embodiment pertains to a vaginal endoscopic surgical blockage to the innervation of prescaral nerve plexus, particularly referring to an operative endoscope inserted through the post fornix of vagina to the retroperitoneal space where the presacral nerve plexus are located, and surgical intervention is used for interfering the afferent and efferent neurons of said presacral nerve plexus.

2 Claims, 2 Drawing Sheets

VAGINAL ENDOSCOPIC SURGICAL BLOCKAGE TO THE INNERVATION OF PRESCARAL NERVE PLEXUS

BACKGROUND OF THE INVENTION

The preferred embodiment proposed by this patent claim pertains to an endoscopic surgical blockage to the innervation of prescaral nerve plexus through vaginal approach, particularly referred to a laparascopic surgical blockage to the innervation of hypogastric nerve plexus or prescaral nerve plexus through the abdomen of lower technical difficulty and higher in safety.

DESCRIPTION OF THE PRIOR ART

Notwithstanding that chronic pelvic floor pain has long been a common issue confronting the gynecological field, which the cause behind chronic pelvic floor pain, except organic mutation, can persist despite no organic mutation ever detected. In clinical practice, hormones may be dispensed as treatment by medication for improving the symptoms, or surgical procedure may be administered in removing the patient's neural plexus.

Conventional laparatomic neurectomy of hypogastric plexus requires surgically removing the hypogastric plexus, a procedure effective in eliminating the patient's symptoms of inorganic pain for said hypogastric plexus are behind the symptoms or inorganic pain suffered by the patient; however, such laparatomic neurectomy comes with wider incision to require the patient in longer-hospital stay, and of slower recovery.

To compensate the downfall of extended incision required of conventional laparatomic neurectomy, an abdominal endoscopic blockage to the innervation of prescaral nerve plexus has been proposed, which requires a surgical procedure of inserting an abdominal endoscope below the patient's navel, locate the hypogastric plexus for surgical removal to minimize the incision and speed up the patient's recovery.

Nevertheless, the laparascopic neurectomy of hypogastric plexus requires infusing $CO_2$ into the patient's abdominal cavity in order to have distended abdominal cavity and better visual assessment of the operative field, which is regarded of higher technical difficulty thus more risky, thus can be improved upon.

SUMMARY OF THE INVENTION

The main objective of the preferred embodiment proposed by the patent lies offering a solution to the problem described above through a vaginal endoscopic surgical blockage to the innervation of prescaral nerve plexus, which pertains to having said vaginal endoscope penetrate the post fornix of vagina to reach the prescaral nerve plexus. The vaginal endoscope is used to locate and surgically intervene the prescaral never plexus which cause the pelvic floor pain. Since posterior fornix of vagina is located closer to the retroperitoneal space, it is easier to locate prescaral nerve plexus by penetrating the post fornix of vagina by the vaginal endoscope for a smaller and shallower incision, thus achieving a dual effect of reduced surgical difficulty and improved safety.

The preferred embodiment proposed by the patent pertains to a vaginal endoscopic surgical blockage to the innervation of prescaral nerve plexus, which entails the following procedure, The patient is prepared in a lithiotomy position or a knee-chest position, and the operation proceeded under proper anesthesia;

Sterilization of operating field is administered to the patient;

The cervix is lifted to expose the post fornix, and the operative vaginal endoscope is inserted through the post fornix of vagina to the retroperitoneal space where the prescaral nerve plexus are located. And since the retroperitoneal space is connected beneath the culdesac pouch, thus no penetration to the retroperitoneal space is needed to enter the pelvic cavity.

The vaginal endoscope is used to locate the innervation of prescaral nerve plexus, and the surgical tool within the vaginal endoscope is used to intervene the innervation of prescaral nerve plexus;

The vaginal endoscope is then retrieved, and a post surgery examination and bleeding treated to conclude the procedure.

DETAILED DESCRIPTION OF THE INVENTION

Figure 1:
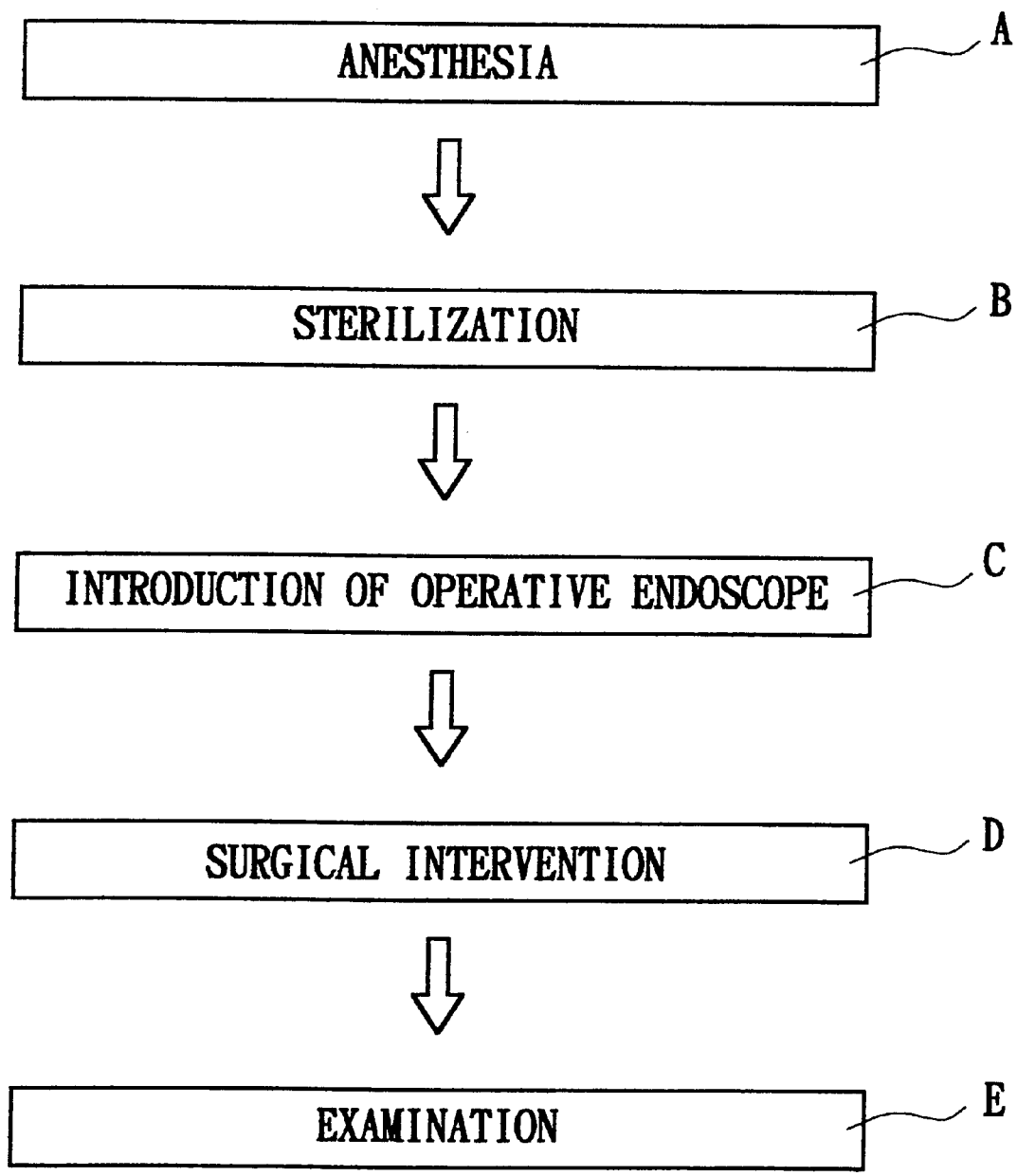
FIG. 1 indicates a surgical diagram proposed by the patent.
Figure 2:
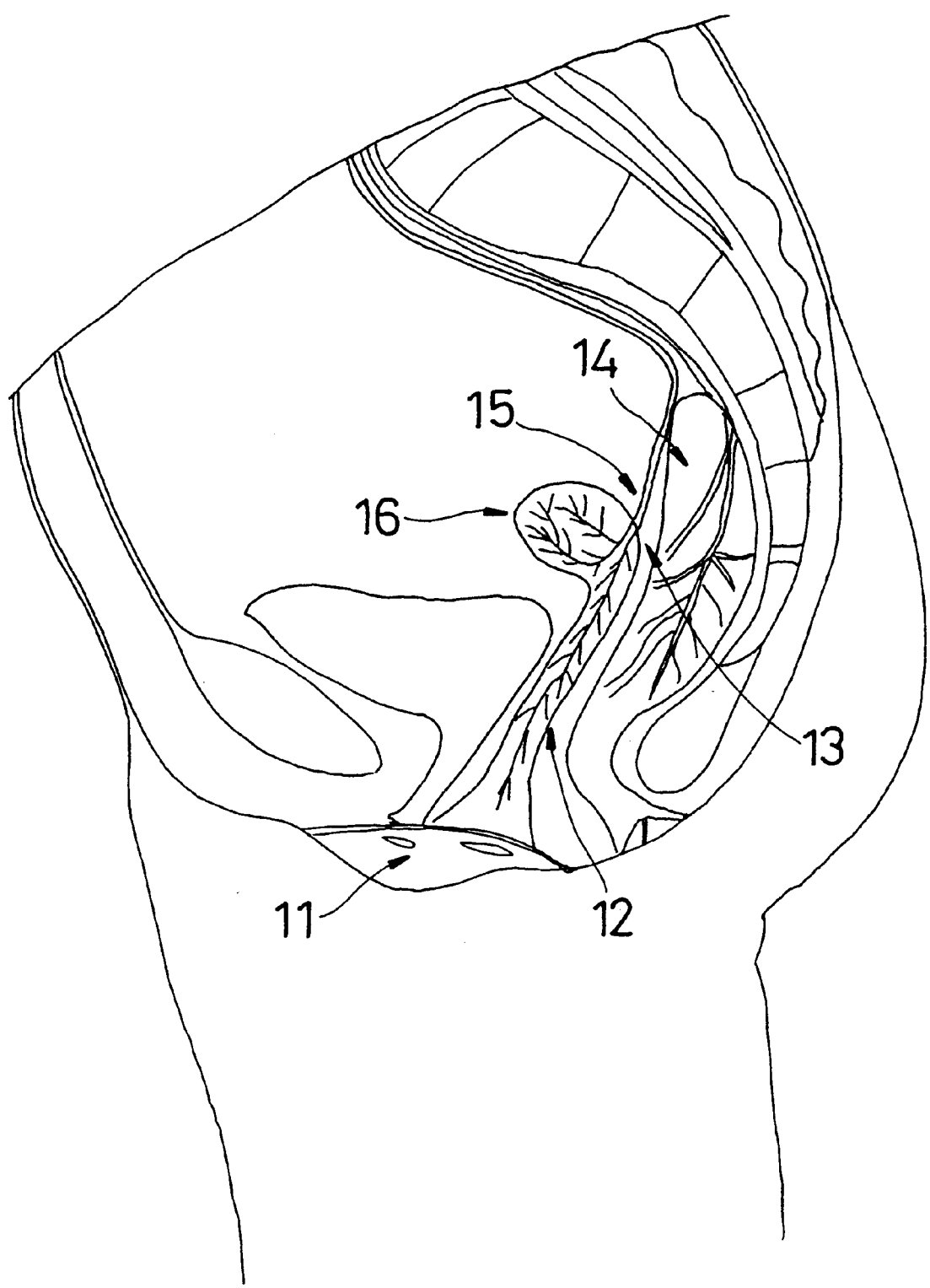
FIG. 2 indicates a perspective view of human organs in and around the abdominal cavity and pelvis.

As provided in FIGS. 1 and 2, the preferred embodiment proposed by the patent pertains to a vaginal endoscopic surgical blockage to the innervation of prescaral nerve plexus, which consists of the following procedure, Step A—anesthesia: The patient is placed in either a lithiotomy position or a knee-chest position, and proper anesthesia is given depending on the patient's physical conditions.

Step B—sterilization: Sterilization is administered to the patient's ext. genital 11 and vagina 12 where surgical procedure is to take place.

Step C—introducing the operative endoscope through the vagina: A cervical crimp is inserted into post fornix of vagina 12 where the cervix is lifted, exposing the post fornix. The operative vaginal endoscope is then inserted into post fornix of vagina 12 to the retroperitoneal space, beneath the uterorectal pouch 13 (culdesac pouch) connectives of the retroperitoneal space, which is right beneath, without having to penetrate the uterorectal pouch to reach the pelvis cavity.

Step D—Surgical intervention: Within the connectives between the uterorectal 13 and uterorectal walls 14, the vaginal endoscope is used to locate afferent and efferent neurons among the prescaral never plexus, which are intervened by the surgical tools within the vaginal endoscope to surgical intervene afferent and efferent neurons which trigger pelvic floor pain by neural blockage or electrolysis disabling the prescaral nerve plexus. Meanwhile, common innervation of prescaral never plexus generally consist of utero vaginal plexus, pelvic plexus and inferior hypogastric plexus; steps involved in the intervention of the innervation of prescaral nerve plexus consist of, 1. Separately locate the utero vaginal plexus at the two sides and sequentially surgical intervene the utero vaginal plexus;
2. Separately locate the pelvic plexus at the two sides and sequentially surgical intervene the pelvic plexus;
3. Separately locate the interior hypogastric plexus at the two sides and sequentially surgical intervene the interior hypogastric plexus.

Step E—examination: Upon removing the vaginal endoscope, examination is taken and bleeding spots treated to conclude the procedure.

The presacral nerve plexus being located between the uterus 16 and rectum 15 near the uterorectal 13, an operative vaginal endoscope 12 is inserted to the retroperitoneal space 13 for easy locating of the patient's presacral nerve plexus. This technique greatly reduces the technical difficulty in surgery and safer, besides the fact that the incision wound left by a vaginal endoscope within the post fronix of vagina tend to be small and shallower, thus allowing speedier recovery. In all, the vaginal endoscopic surgical blockage to the innervation of presacral nerve plexus proposed by the patent can bring forth a dual property of effectively reducing the surgical difficulty and improving the safety.

TECHNICAL SUMMATION

1. The conventional procedure of laparascopic presacral neurectomy invariably involves the following process, Endoscope inserted→accessing the abdominal cavity→infusing CO2→accessing the retroperitoneal space→neurectomy performed.
2. Whereas, the vaginal endoscopic neuro blockage provides a simpler procedure, Vaginal endoscope inserted→quick access to the retroperitoneal space, without having to penetrate the abdominal cavity→surgical intervention performed.

What is claimed is:

1. A method of vaginal endoscopic surgical blockage to an innervation of a patient's presacral nerve plexus, the method comprising the steps of:
   (a) placing a patient in one of a lithotomy position or a knee-chest position;
   (b) administering anesthesia to the patient;
   (c) sterilizing the operative field;
   (d) lifting the patient's cervix to expose the patient's post fornix;
   (d) inserting an operative vaginal endoscope through the post fornix to connective tissue beneath the patient's uterorectal pouch without penetrating the uterorectal pouch;
   (e) advancing the operative vaginal endoscope to locate the innervation of the patient's presacral nerve plexus;
   (f) using a surgical tool of the operative vaginal endoscope to intervene in the innervation of the nerve plexus located in step (e); and,
   (g) removing the operative vaginal endoscope and treating vaginal bleeding of the patient.
2. The method as recited in claim 1, wherein the step of advancing the operative vaginal endoscope includes the step of separately locating the patient's uterovaginal plexus, pelvic plexus, and inferior hypogastric plexus.

* * * * *